United States Patent
Brody et al.

(10) Patent No.: US 11,813,125 B2
(45) Date of Patent: Nov. 14, 2023

(54) INSTRUMENT CLEANING ASSEMBLIES AND RELATED METHODS

(71) Applicant: C-Clear, LLC, Midvale, UT (US)

(72) Inventors: Fredrick Brody, Bethesda, MD (US); Wayne Shortt, Midvale, UT (US); Matt Penny, Holly Springs, NC (US)

(73) Assignee: C-Clear, LLC, Midvale, UT (US)

( * ) Notice: Subject to any disclaimer, the term of this patent is extended or adjusted under 35 U.S.C. 154(b) by 850 days.

(21) Appl. No.: 16/598,788

(22) Filed: Oct. 10, 2019

(65) Prior Publication Data

US 2021/0106401 A1    Apr. 15, 2021

(51) Int. Cl.
*A61B 90/70* (2016.01)
*B08B 1/00* (2006.01)
*A61B 90/00* (2016.01)

(52) U.S. Cl.
CPC .............. *A61B 90/70* (2016.02); *B08B 1/001* (2013.01); *A61B 2090/3966* (2016.02); *A61B 2090/701* (2016.02)

(58) Field of Classification Search
CPC .............. A61B 90/70; A61B 2090/701; A61B 2090/3966; B08B 1/001; B08B 1/003; B08B 1/006; A47L 13/12
See application file for complete search history.

(56) References Cited

U.S. PATENT DOCUMENTS

| | | |
|---|---|---|
| 2,810,150 A | 10/1957 | Ellman |
| 3,021,649 A * | 2/1962 | Robbins ................ B24D 15/04 |
| | | 15/118 |
| 3,058,139 A | 10/1962 | Eva |
| 3,317,944 A * | 5/1967 | Napier ................... B05C 17/00 |
| | | 15/244.1 |
| 3,694,845 A * | 10/1972 | Engelsher ............... A47K 7/02 |
| | | 15/244.4 |
| 4,856,136 A | 8/1989 | Janssen |
| 4,866,806 A * | 9/1989 | Bedford .................. A47L 13/16 |
| | | 15/244.4 |
| 5,010,615 A | 4/1991 | Carter |
| 5,212,847 A | 5/1993 | Melcher et al. |
| 5,295,952 A | 3/1994 | Pietrafitta |
| 5,382,297 A * | 1/1995 | Valentine ............... A61B 1/127 |
| | | 15/210.1 |
| 5,514,084 A | 5/1996 | Fisher |
| 5,548,862 A | 8/1996 | Curtis |
| 5,799,357 A | 9/1998 | Taylor |
| 5,922,003 A | 7/1999 | Anctil |

(Continued)

FOREIGN PATENT DOCUMENTS

WO    WO 2015/013513 A1    1/2015

*Primary Examiner* — Randall E Chin
(74) *Attorney, Agent, or Firm* — Thorpe North & Western; Jason R. Jones

(57) ABSTRACT

An assembly for cleaning a surgical instrument includes a first cleaning segment and a second cleaning segment coupled thereto. The first and second cleaning segments each present a respective first and second cleaning interface configured to be contacted by a first surgical instrument to clean a portion of the first surgical instrument. The first and second cleaning segments collectively define an instrument receiving channel sized and shaped to receive therein a second surgical instrument to thereby secure the first and second cleaning segments to the second surgical instrument.

10 Claims, 11 Drawing Sheets

(56) References Cited

U.S. PATENT DOCUMENTS

| | | | |
|---|---|---|---|
| 8,001,645 B2* | 8/2011 | Kaufman | A61B 90/70 |
| | | | 15/244.4 |
| 8,196,248 B2* | 6/2012 | Kritzler | C11D 3/046 |
| | | | 15/115 |
| 10,114,216 B2 | 10/2018 | Brody | |
| 2001/0016962 A1 | 8/2001 | Moore | |
| 2002/0166190 A1 | 11/2002 | Miyake | |
| 2009/0113644 A1 | 5/2009 | Heck | |
| 2013/0035671 A1 | 2/2013 | Brand et al. | |
| 2013/0228196 A1 | 9/2013 | Vazales | |
| 2016/0022367 A1 | 1/2016 | Brody | |
| 2016/0175065 A1 | 6/2016 | Gomez et al. | |
| 2017/0095840 A1 | 4/2017 | Pisacane | |
| 2017/0215986 A1 | 8/2017 | Brody et al. | |
| 2018/0014907 A1 | 1/2018 | Sweeney | |
| 2018/0372981 A1 | 12/2018 | Lane | |

* cited by examiner

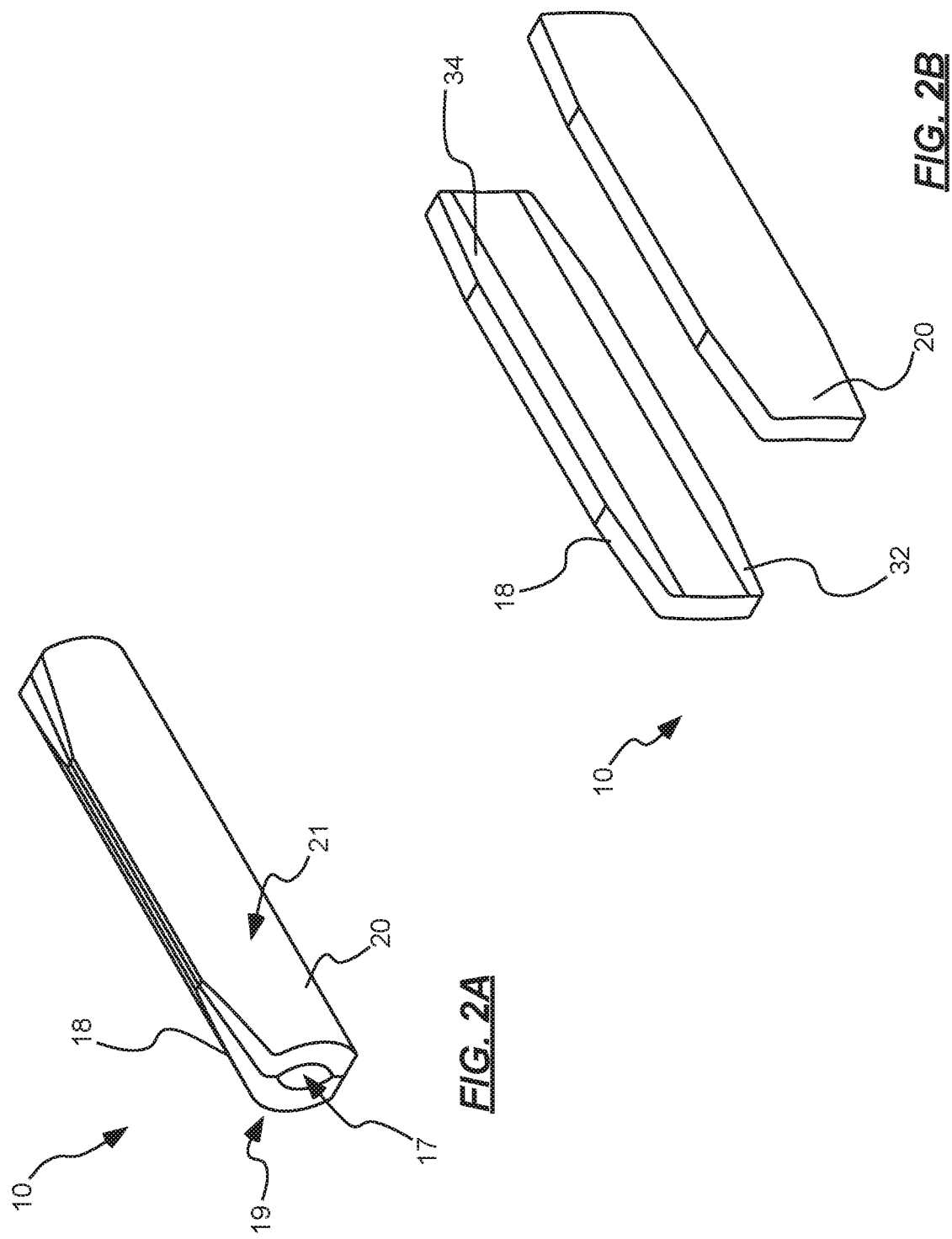

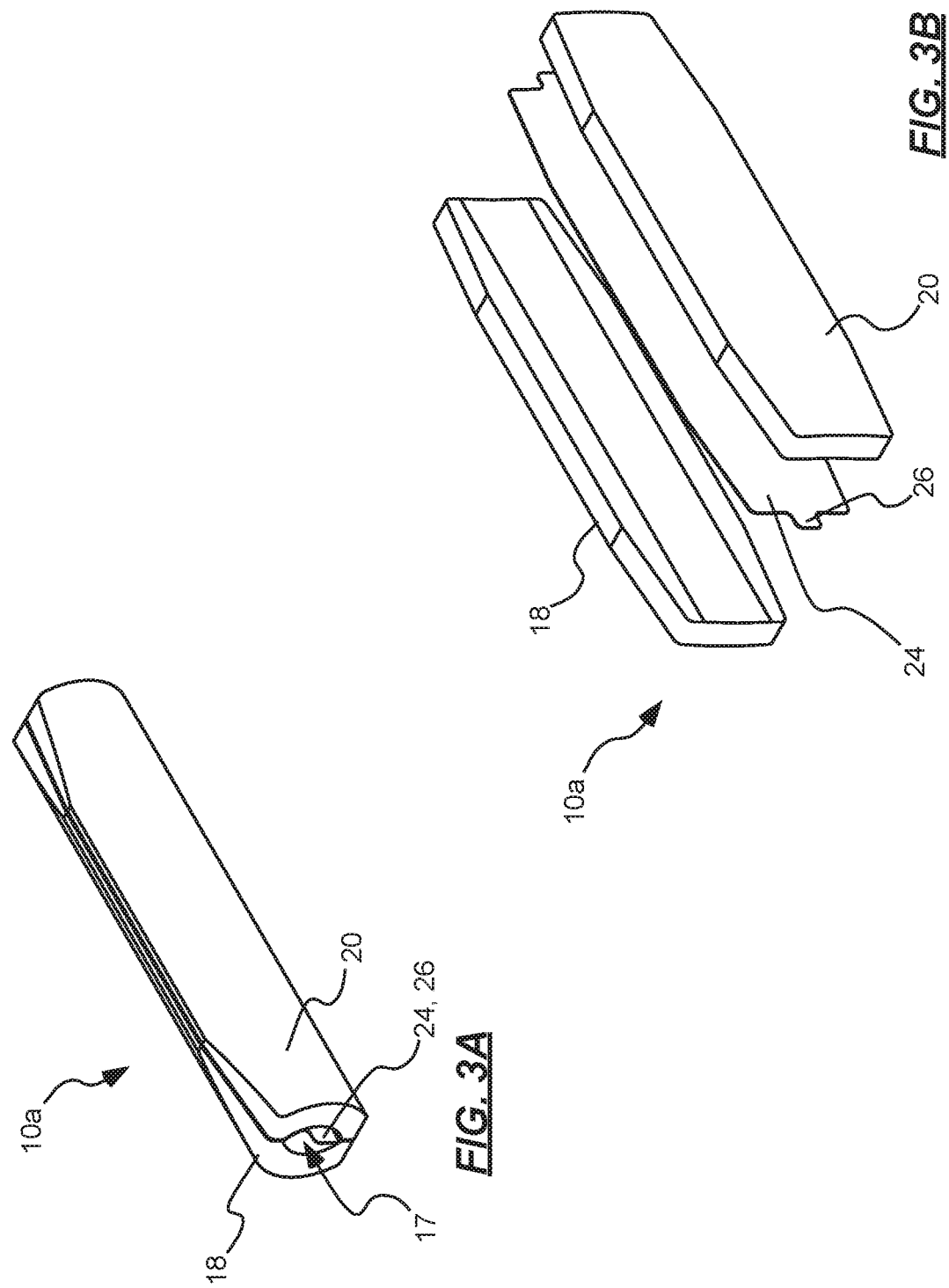

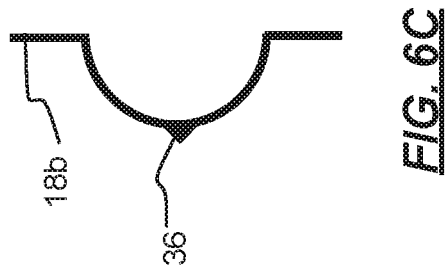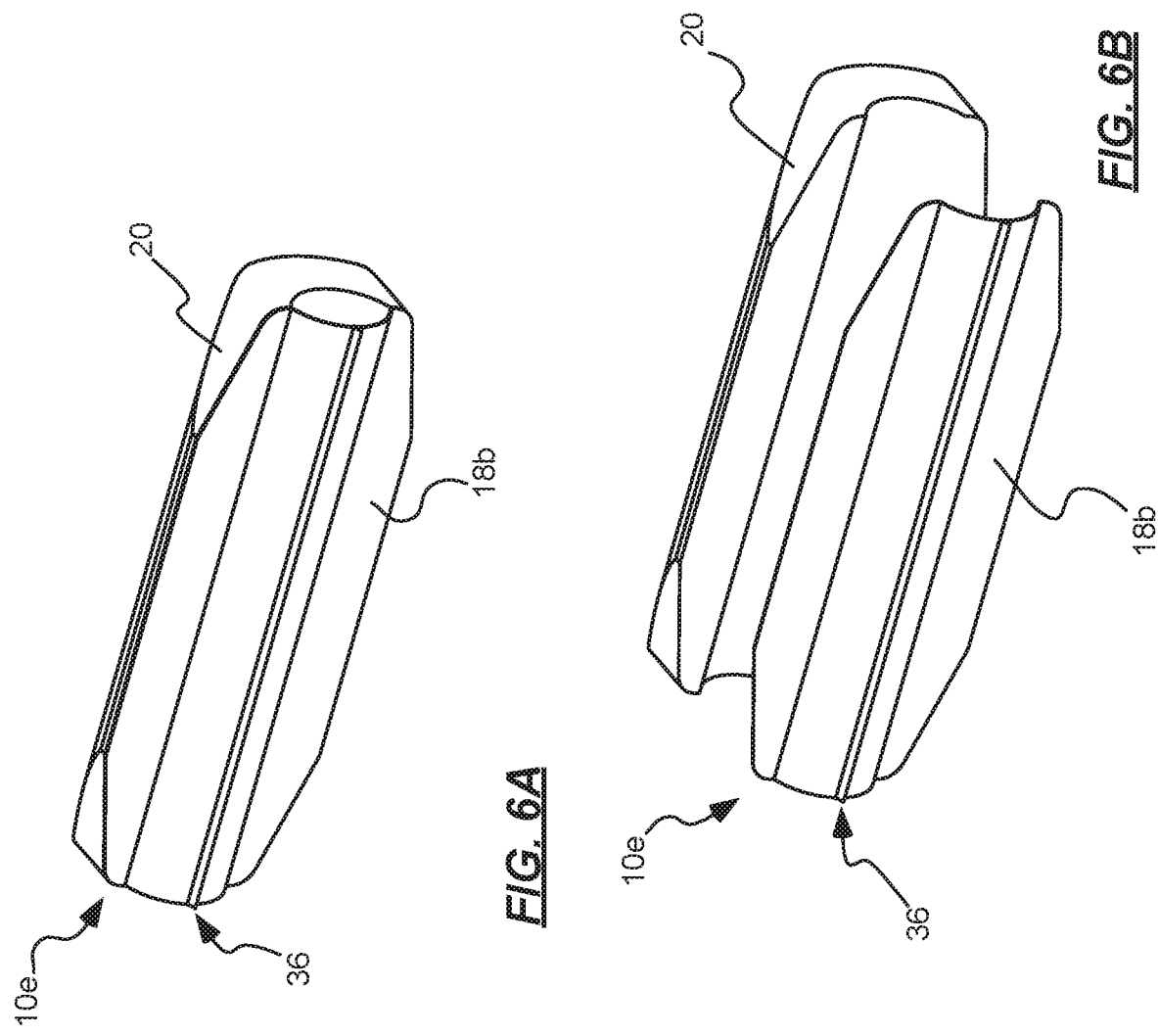

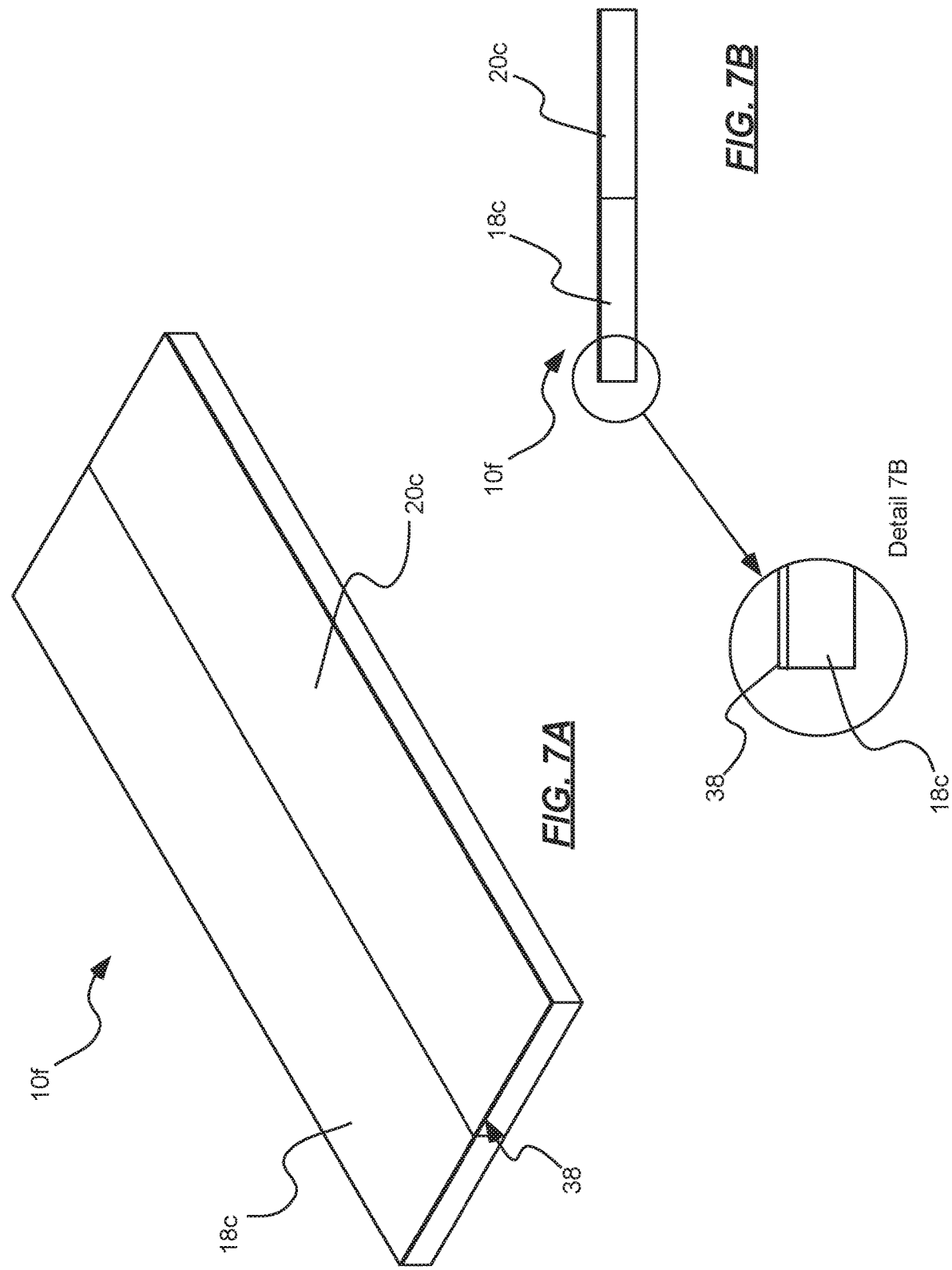

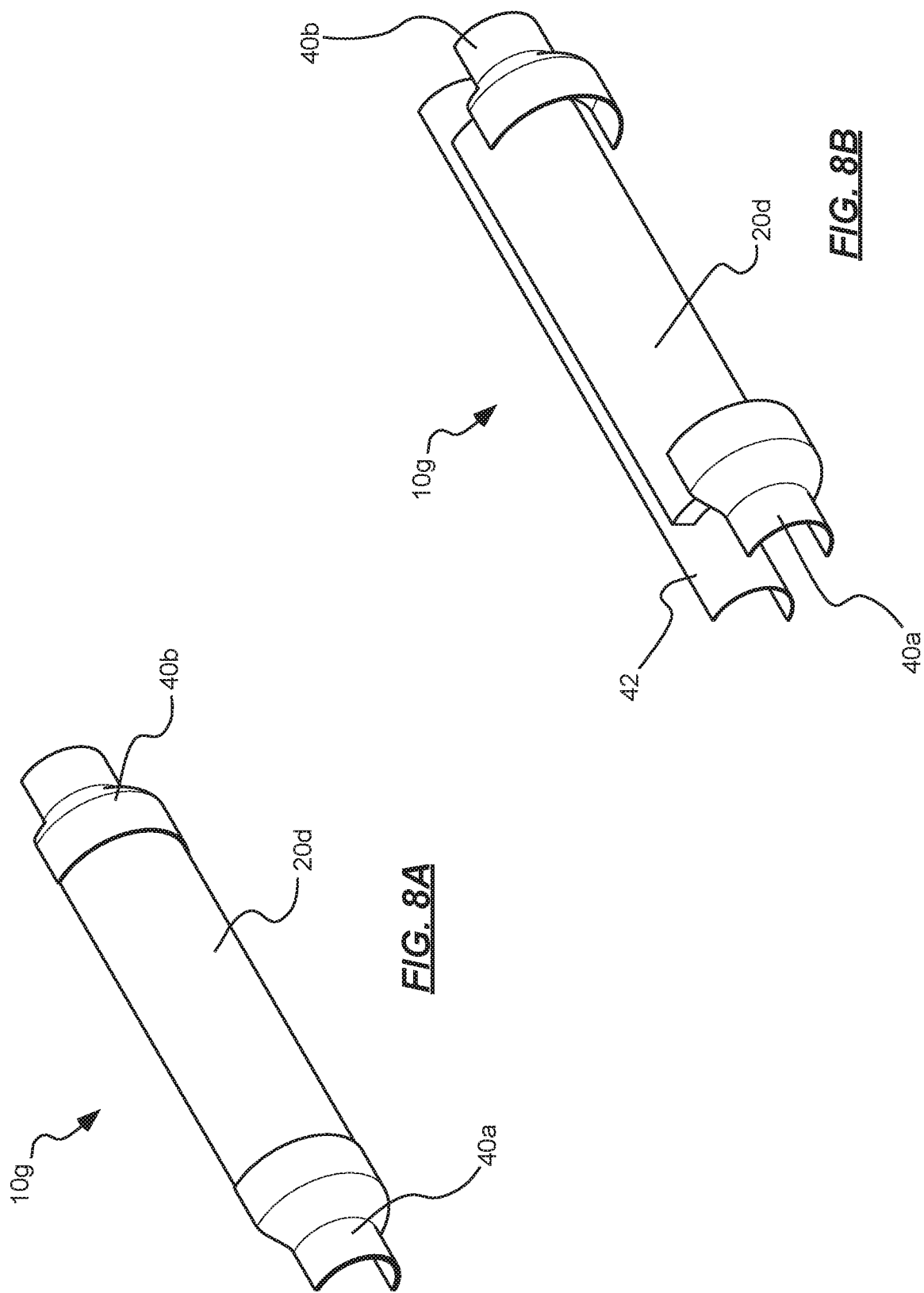

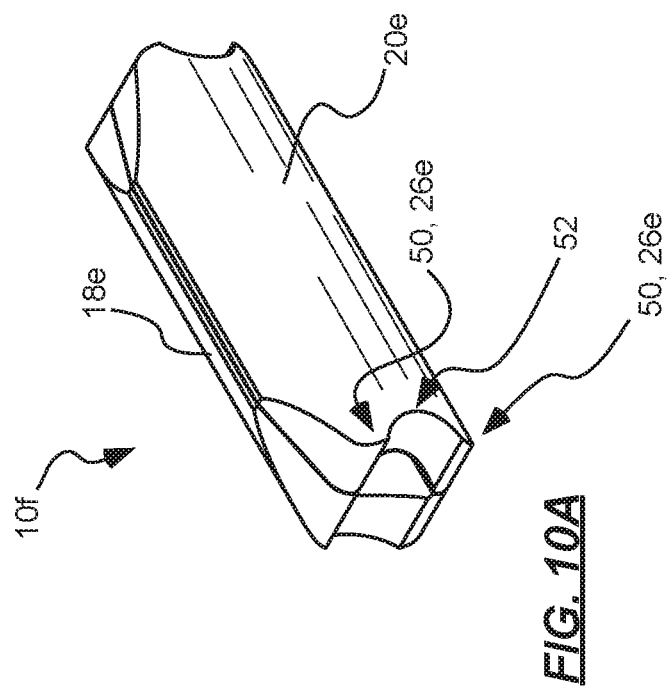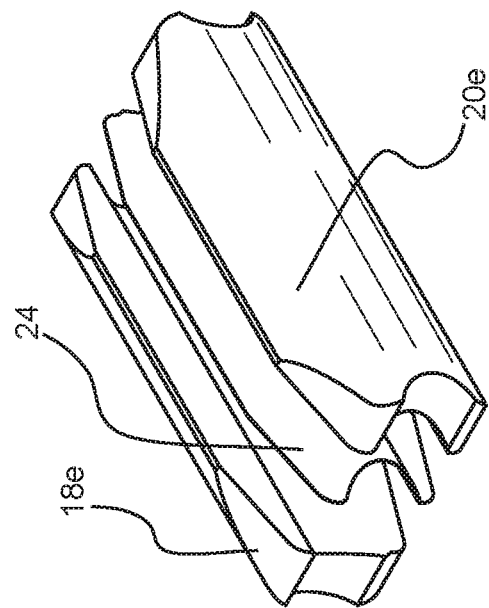

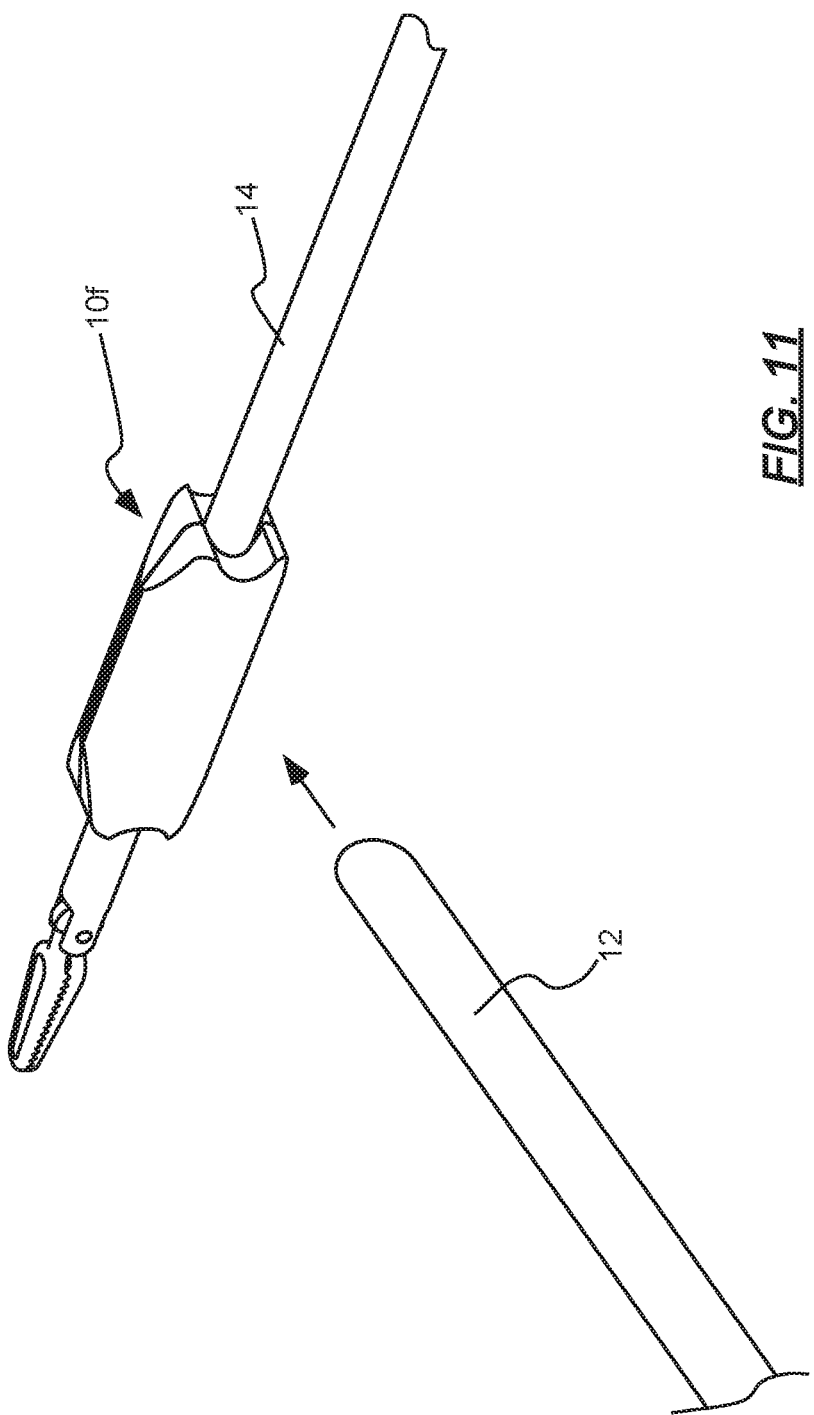

INSTRUMENT CLEANING ASSEMBLIES AND RELATED METHODS

BACKGROUND OF THE INVENTION

Field of the Invention

The present technology relates generally to systems and methods for cleaning surgical instrumentation, including scope lenses, during minimally invasive procedures.

Related Art

Minimally invasive procedures have been used for some time to minimize the size of incisions required for surgical procedures. Compared to conventional, open surgeries, minimally invasive procedures provide lower post-operative healing times, with shorter convalescence periods and decreased risks. While minimally invasive procedures provide many benefits, they suffer from some difficulties due to limited visibility inside the body cavity. These procedures typically involve making small incisions to introduce equipment and scopes into the body cavity in order to perform complicated medical procedures, such as ligating, cutting, clamping, suturing, and/or repairing tissue. Consequently, these procedures require excellent visualization obtained through the scope introduced into the body cavity.

One of the most common problems that prolongs the minimally invasive procedure is associated with maintaining continued visibility via the scope. After inserting the scope into the body cavity, the lens can become obstructed due to smudging, condensation, and/or direct contact with body tissue and fluids. In order to provide the surgeon with a clear view, the scope often needs to be removed from the body cavity, cleaned, and then reinserted. This can substantially lengthen the procedure and possibly lead to other complications.

SUMMARY OF THE INVENTION

In accordance with one aspect of the technology, an assembly is provided for cleaning a surgical instrument. The assembly can include a first cleaning segment and a second cleaning segment, coupled to the first cleaning segment. The first and second cleaning segments can present a respective first and second cleaning interface configured to be contacted by a first surgical instrument to clean a portion of the first surgical instrument. The first and second cleaning segments can collectively define an instrument receiving channel sized and shaped to receive therein a second surgical instrument to thereby secure the first and second cleaning segments to the second surgical instrument.

In accordance with another aspect of the technology, an assembly is provided for cleaning a surgical instrument. The assembly can include a first cleaning segment and a second cleaning segment, coupled to the first cleaning segment. The first and second cleaning segments can present a respective first and second cleaning interface configured to be contacted by a first surgical instrument to clean a portion of the first surgical instrument. The first cleaning interface can differ from the second cleaning interface so as to provide at least two differing cleaning interfaces for cleaning the first surgical instrument. The first and second cleaning segments can collectively define an instrument receiving channel sized and shaped to receive therein a second surgical instrument to thereby secure the first and second cleaning segments to the second surgical instrument.

In accordance with another aspect of the technology, a method of forming an assembly for cleaning a surgical instrument is provided. The method can include obtaining a first cleaning segment and a second cleaning segment, the first and second cleaning segments presenting a respective first and second cleaning interface configured to be contacted by a first surgical instrument to clean a portion of the first surgical instrument. The first cleaning interface can differ from the second cleaning interface so as to provide at least two differing cleaning interfaces for cleaning the first surgical instrument. The method can include coupling the first cleaning segment to the second cleaning segment to thereby define an instrument receiving channel between the first and second cleaning segments. The instrument receiving channel can be sized and shaped to receive therein a second surgical instrument to thereby secure the first and second cleaning segments to the second surgical instrument.

BRIEF DESCRIPTION OF THE DRAWINGS

The following drawings illustrate exemplary embodiments for carrying out the invention. Like reference numerals refer to like parts in different views or embodiments of the present invention in the drawings.

FIG. 2A is a perspective view of a cleaning assembly in accordance with the present technology;

FIG. 2B is an exploded view of the cleaning assembly of FIG. 2A;

FIG. 3A is a perspective view of another cleaning assembly in accordance with the present technology;

FIG. 3B is an exploded view of the cleaning assembly of FIG. 3A;

FIG. 6A is a perspective view of another cleaning assembly in accordance with the present technology;

FIG. 6B is an exploded view of the cleaning assembly of FIG. 6A;

FIG. 6C is an end view of one cleaning segments of the cleaning assembly of FIG. 6A;

FIG. 7A is a perspective view of another cleaning assembly in accordance with the present technology;

FIG. 7B is an end view of the cleaning assembly of FIG. 7A;

FIG. 8A is a perspective view of another cleaning assembly in accordance with the present technology;

FIG. 8B is an exploded view of the assembly of FIG. 8A;

FIG. 10A is a perspective view of a cleaning assembly in accordance with another aspect of the technology;

FIG. 10B is a partially exploded view of the cleaning assembly of FIG. 10A; and FIG. 11 is a perspective view of the cleaning assembly of FIG. 10A installed about a second surgical instrument.

DETAILED DESCRIPTION

Figure 1:
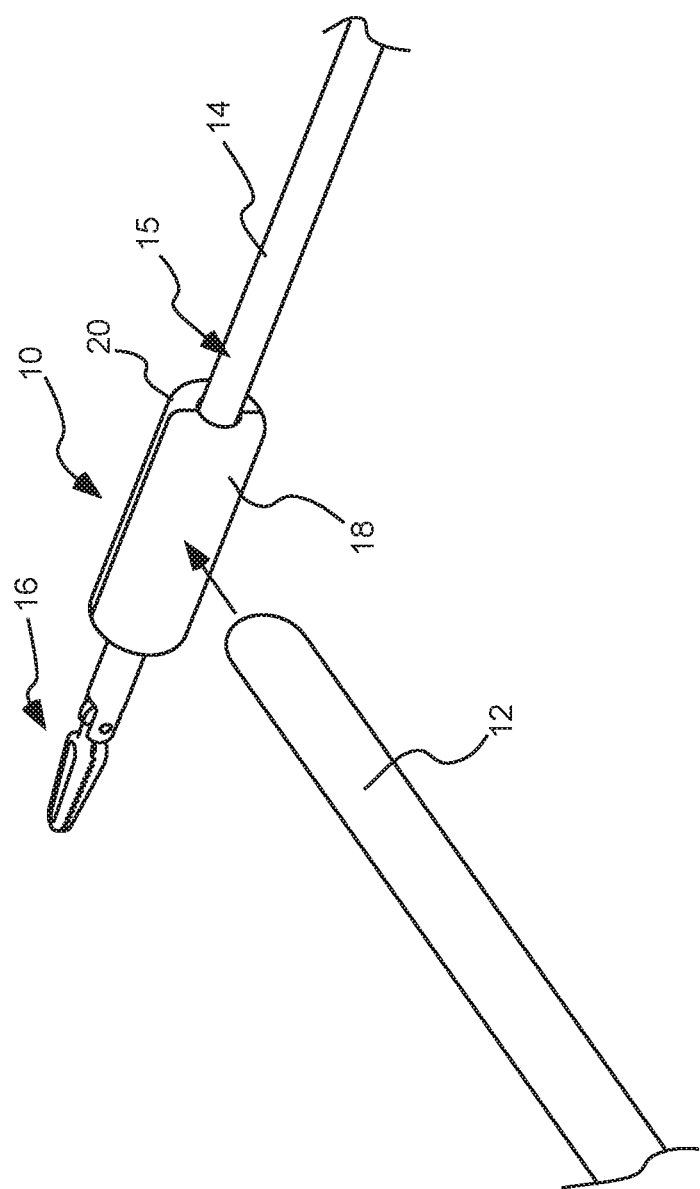
FIG. 1 is a perspective view of a first and second surgical instrument, with a cleaning assembly carried by the second surgical instrument configured to clean the first surgical instrument.

Reference will now be made to the exemplary embodiments illustrated in the drawings, and specific language will be used herein to describe the same. It will nevertheless be understood that no limitation of the scope of the invention is thereby intended. Alterations and further modifications of the inventive features illustrated herein, and additional applications of the principles of the inventions as illustrated herein, which would occur to one skilled in the relevant art and having possession of this disclosure, are to be considered within the scope of the invention.

Definitions

As used herein, the singular forms "a" and "the" can include plural referents unless the context clearly dictates otherwise. Thus, for example, reference to "a cleaning interface" can include one or more of such interfaces, if the context so dictates.

As used herein, the term "substantially" refers to the complete or nearly complete extent or degree of an action, characteristic, property, state, structure, item, or result. As an arbitrary example, an object that is "substantially" enclosed is an article that is either completely enclosed or nearly completely enclosed. The exact allowable degree of deviation from absolute completeness may in some cases depend upon the specific context. However, generally speaking the nearness of completion will be so as to have the same overall result as if absolute and total completion were obtained. The use of "substantially" is equally applicable when used in a negative connotation to refer to the complete or near complete lack of an action, characteristic, property, state, structure, item, or result. As another arbitrary example, a composition that is "substantially free of" an ingredient or element may still actually contain such item so long as there is no measurable effect as a result thereof.

As used herein, the term "about" is used to provide flexibility to a numerical range endpoint by providing that a given value may be "a little above" or "a little below" the endpoint.

Relative directional terms can sometimes be used herein to describe and claim various components of the present invention. Such terms include, without limitation, "distal," "proximal," "upward," "downward," "horizontal," "vertical," etc. These terms are generally not intended to be limiting, but are used to most clearly describe and claim the various features of the invention. Where such terms must carry some limitation, they are intended to be limited to usage commonly known and understood by those of ordinary skill in the art in the context of this disclosure. In some instances, dimensional information is included in the figures. This information is intended to be exemplary only, and not limiting. In some cases, the drawings are not to scale and such dimensional information may not be accurately translated throughout the figures.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 to about 5" should be interpreted to include not only the explicitly recited values of about 1 to about 5, but also include individual values and sub-ranges within the indicated range. Thus, included in this numerical range are individual values such as 2, 3, and 4 and sub-ranges such as from 1-3, from 2-4, and from 3-5, etc., as well as 1, 2, 3, 4, and 5, individually.

This same principle applies to ranges reciting only one numerical value as a minimum or a maximum. Furthermore, such an interpretation should apply regardless of the breadth of the range or the characteristics being described.

Invention

The present technology relates generally to apparatuses and related methods for cleaning surgical instruments. More particularly, the technology relates to such systems that can be used intraoperatively, within a body cavity. As shown generally in FIG. 1, in one aspect of the technology, an assembly 10 can be provided for cleaning a surgical instrument. In the embodiment shown, the assembly can be used to clean a first surgical instrument 12 and can be carried by, or attached to, a second surgical instrument 14. While the invention described herein is not so limited, in the examples shown the first surgical instrument 12 can be a scope or other optical device that requires at least limited visual capability within a body cavity to function well. The first surgical instrument is sometimes referenced herein generically as a "scope," with the understanding that such terminology is merely exemplary.

The second surgical instrument 14 can be any of a variety of instruments used in a surgical procedure, including without limitation, instruments used for clamping, cutting, suturing, ligating, etc. Generally speaking, the second surgical instrument includes an elongate body portion 15 about which the cleaning assembly 10 is secured or attached or held. During use, the lens of the scope 12 can oftentimes become occluded due to buildup of vapor, condensation, fluids, body tissue, etc., on the lens. Removing the scope from the body cavity for cleaning can be very time consuming and disruptive to the surgical procedure. The present technology allows a surgeon or support staff to clean the lens of the scope on the cleaning assembly 10 without removing either surgical instrument from the body cavity.

In the example shown in FIGS. 1, 2A and 2B, the assembly 10 can include a first cleaning segment 18 and a second cleaning segment 20, coupled to the first cleaning segment. The two cleaning segments, once coupled together, collectively define a cleaning assembly. The first cleaning segment can present a first cleaning interface, shown generally at 19 (FIG. 2A), and the second cleaning segment can present a second cleaning interface, shown generally at 21 (FIG. 2A). Each of these cleaning interfaces can be configured to be contacted by the first surgical instrument 12 to clean at least a portion of the first surgical instrument. The first and second cleaning segments can collectively define an instrument receiving channel (17 in FIG. 2A). The receiving channel can be sized and shaped to receive therein the body 15 of the second surgical instrument 14 to thereby secure the first and second cleaning segments to the second surgical instrument.

The manner in which the cleaning assembly 10 is secured to or carried by the second surgical instrument 14 can vary. In one embodiment, the material of at least one of the first and second cleaning segments 18, 20, which collectively form the instrument receiving channel 17, can be at least partially elastic. In this manner, as the cleaning assembly is slidably positioned along the body 15 of the second surgical instrument 14, one or both of the materials of the first and second cleaning segments can elastically expand. This elastic expansion results in the cleaning assembly being held snugly about the body 15 and prevented from moving under the relatively light load applied while cleaning the scope 12. The elastic interface, however, is sufficiently weak that an operator can easily slide the cleaning assembly along the body 15 to install, position, reposition and/or remove the cleaning assembly, as desired. This design enables, in some embodiments, the material of the first and/or second cleaning segment to directly contact the body of the scope. This aspect can allow attachment of the assembly without requiring any intervening structure, which could otherwise increase a cost, weight and size of the device.

In some embodiments, the first cleaning interface 19 can differ from the second cleaning interface 21 so as to provide at least two differing cleaning interfaces for cleaning the scope 12. The cleaning interfaces can be varied in a number of manners. In one aspect, the cleaning segments are formed from materials that exhibit differing material properties. For example, the first cleaning segment can be formed from a material that is more porous than the second cleaning segment, or more abrasive, softer or harder, tougher, or more or less absorbent, hydrophilic vs. hydrophobic, to name a few. A surgeon may find, for example, depending upon the unwanted material that has collected on the scope lens, that the first cleaning segment is better suited to remove fluids or particulates from the scope lens, while the second cleaning segment is better suited to remove vapor deposits from the lens.

The differences in material properties can be accomplished in a variety of manners. For example, the material from which each of the first 18 and second 20 cleaning segments are formed can be varied. A manner in which or by which the segments are treated can also be varied. For example, one material can be treated with a finish that affects it toughness, porosity, hardness, etc. The materials may, for example, share the same base structure but differ in some manner. For example, each may be formed from the same polymeric material, but one segment may be provided with a higher degree of porosity. A surface of one or both of the segments may be treated with an additional material that alters the cleaning interface presented by that particular material. For example, a film may be applied to the surface of one of the segments that results in that segment being hydrophobic, while the other segment remains hydrophilic. Any of a variety of known materials and material formation, material finishing techniques, etc., can be utilized to form or alter or condition the differing cleaning interfaces presented.

The manner in which first 18 and second 20 cleaning segments are coupled to one another can vary. As shown by example in FIG. 2B, the segments can initially be provided as two distinct components. Outer or side edges 32, 34 of segment 18 can be coupled to corresponding outer edges of segment 20. In this manner, the resulting instrument receiving channel (17 in FIG. 2A) is formed as an envelope between the two cleaning segments. This envelope can expand from a very thin slit (as shown in FIG. 2B) to a generally cylindrical opening (as shown in FIG. 2A) to receive the body 15 of the second surgical instrument 14.

The manner in which outer edges 32, 34 of segment 18 are coupled to opposing outer edges of segment 20 can vary. In one aspect, the edges are bonded to one another using a suitable adhesive. In another example, a plastic welding technique can be utilized to accomplish the bond. In some of the examples shown, for example, in FIGS. 2A and 2B, the individual segments can be bonded to one another in a rough or partially unfinished form (FIG. 2B). After bonding, the assembly can be machined or otherwise finished to create the more rounded profile shown in the finished assembly (FIG. 2A). The individual components can also be machined or smoothed prior to assembly, if desired.

In the examples shown in FIGS. 3A and 3B, assembly 10a can include an intermediate or buffer layer 24 applied between the first 18 and second 20 cleaning segments. This buffer layer can be advantageous in some embodiments to alter a characteristic of one or both the cleaning segments. Generally, the buffer layer can be positioned adjacent an internal surface of the cleaning segment(s) so as to alter a characteristic of the cleaning segment(s) within or adjacent the instrument receiving channel (17, FIG. 3A). The buffer layer can add strength to the assembly, can decrease a surface friction in the interface between surgical instrument and the cleaning assembly, etc. In one example, the buffer layer can be formed partially or fully from a radiopaque material, such as barium sulfate or the like, to provide visibility in various imaging techniques. The buffer layer can be laminated to one or both of the cleaning segments prior to bonding of the cleaning segments together, or the buffer layer can be attached at the time of bonding the edges of the segments one to another.

In the example shown in FIGS. 3A and 3B, the buffer or intermediate layer 24 can include a protrusion or tab 26 that extends from a body proper of the buffer layer. As shown in FIG. 3A, the tab can protrude from one or both the cleaning segments 18, 20. The tab can provide a convenient and secure location for a user to grasp the cleaning assembly 10a to install, position, reposition or remove the assembly. The tab can allow a surgeon or technician to easily grasp a cleaning segment, even intracorporeally with an instrument during surgery, to reposition or remove and/or install the segment. The tab can extend beyond one end of the assembly, or both ends.

Figure 4B:
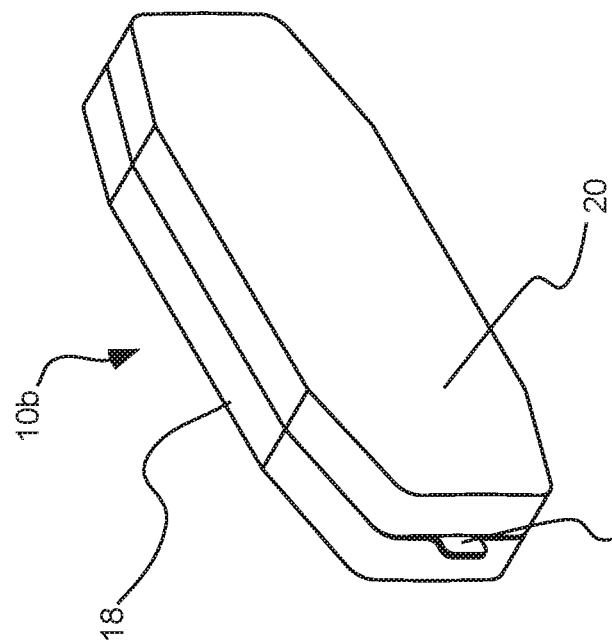
FIG. 4B is an exploded view of the cleaning assembly of FIG. 4A.
Figure 4A:
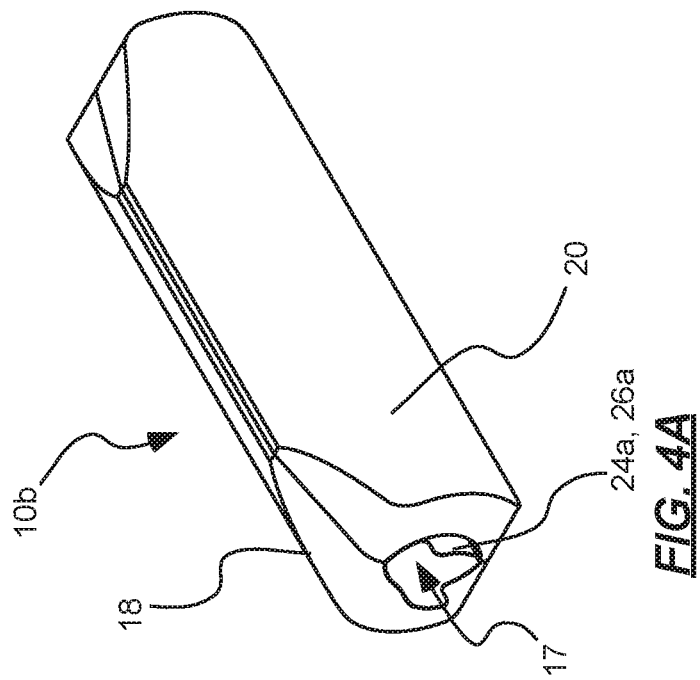
FIG. 4A is a perspective view of another cleaning assembly in accordance with the present technology.

FIGS. 4A and 4B illustrate a further embodiment of the invention in which cleaning assembly 10b includes first 18 and second 20 cleaning segments with a buffer layer 24a that substantially circumscribes the instrument receiving channel 17. The buffer layer 24a can include two tabs 26a that extend outwardly from the cleaning assembly on opposing sides of the receiving channel.

Figure 5B:
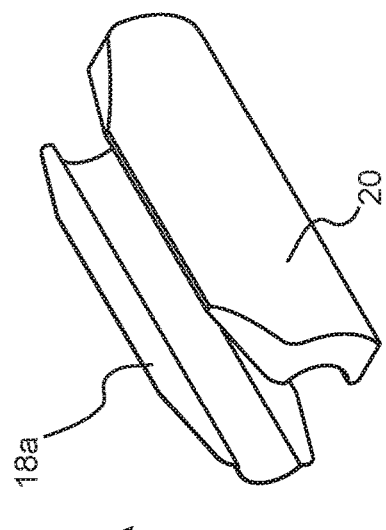
FIG. 5B is an exploded view of the cleaning assembly of FIG. 5A.
Figure 5A:
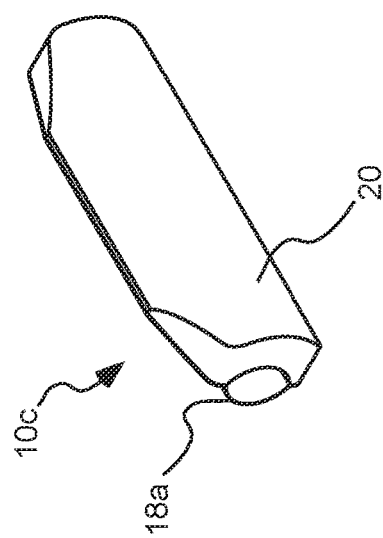
FIG. 5A is a perspective view of another cleaning assembly in accordance with the present technology.
Figure 5C:
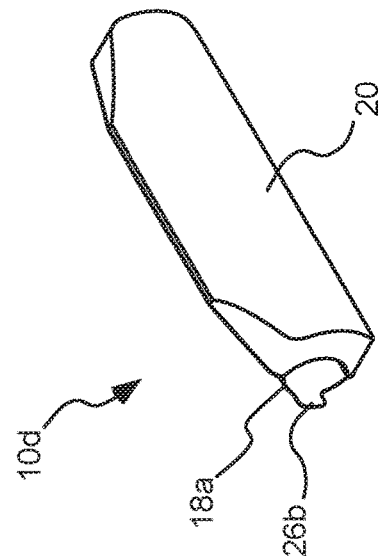
FIG. 5C is a perspective view of an alternate embodiment of the cleaning assembly of FIG. 5A.

In the example shown in FIGS. 5A, 5B and 5C, cleaning segment 18a is formed from a material similar to the buffer layer 24, 24a described above, while cleaning segment 20 is formed in much the same manner as described above. This aspect of the invention can be advantageous in applications where a cleaning assembly 10c is desired to have a smaller cross section, with fewer material costs. In the exemplary cleaning assembly 10d shown in FIG. 5C, cleaning segment 18a includes tab 26b extending therefrom, to provide a convenient location for a user to grasp the cleaning assembly.

FIGS. 6A through 6C illustrate another embodiment wherein first cleaning segment 18b carries a wiper fin 36. The wiper fin can be formed as an integral portion of cleaning segment 18b, or it can be attached thereto in a number of known manners. While not so required, both the wiper fin and cleaning segment 18b can be formed from a polymeric or elastomeric, hydrophilic, relatively rigid material. In this manner, a surgeon can use the wiper fin to cleanly wipe a lens of the scope 12 free from liquids, particulates, vapor, etc.

In the example shown FIGS. 7A and 7B, cleaning assembly 10f can include one or more cleaning segments arranged in a generally planar arrangement. In the embodiment shown, two segments, 18c and 20c are shown arranged side-by-side. It is to be understood, however, that a single cleaning segment can be utilized, or more than two. An adhesive layer 38 can be arranged atop the cleaning segment(s). A removable backing (not shown) can be positioned atop the adhesive layer to protect the adhesive prior to use.

In use, a surgeon or technician can remove the adhesive backing (not shown), thereby exposing the adhesive layer 38. The cleaning assembly can then be applied about the body 15 of a secondary surgical instrument 12 and thereby secured in position about the instrument. This embodiment can be relatively easily positioned by a user. The adhesive of the adhesive backing can be designed so that the cleaning assembly 10f can be relatively easily removed from the instrument and discarded or used again, where appropriate. Outside edges of the segments 18c, 20c may or may not adjoin one another when the assembly is wrapped about the instrument, or they may abut one another or overlap one another. As this embodiment does not require an exact fit about a body of a surgical instrument, it can be used with a variety of different sizes of instruments. This embodiment is also advantageous when a surgical instrument includes relatively large components that prevent a cleaning assembly from being easily slid along the instrument.

In the example shown in FIGS. 8A and 8B, a cleaning assembly 10g is provided that can include one or more cleaning segments 20d arranged in a generally half-cylindrical arrangement. In the embodiment shown, two shields or transitional segments 40a, 40b are positioned at either end of the cleaning segment. An adhesive layer 42 can be arranged beneath the cleaning segment and shields. A portion of each shield can be bonded to the adhesive layer, while the remaining portion of each shield can cover and/or be bonded to a portion of the cleaning segment. The shield or transitional segment can be advantageous in a number of manners. Firstly, the shield can provide visibility to medical imaging technologies via the composition of the shield material. For example, the shield can be partially or fully formed from a radiopaque material that is apparent in a variety of imaging technologies. Secondly, the transitional segment can aid in providing a taper to either or both ends of the cleaning segment to ease introduction of and removal from the abdominal port to prevent damage to or dislodging of the cleaning segment during these processes. The third function is to provide a tab for applying and removing the cleaning assembly from the shaft of a surgical instrument.

Analogously to the embodiments shown and described in relation to FIGS. 7A and 7B, the cleaning assembly 10g of FIGS. 8A and 8B can be removably attached to a surgical instrument. A removable backing (not shown) can be positioned atop the adhesive layer to protect the adhesive prior to use. In use, a surgeon or technician can remove the adhesive backing (not shown), thereby exposing the adhesive layer 42. The cleaning assembly can then be applied about the body of a secondary surgical instrument and be thereby secured in position about the instrument.

Figure 9A:
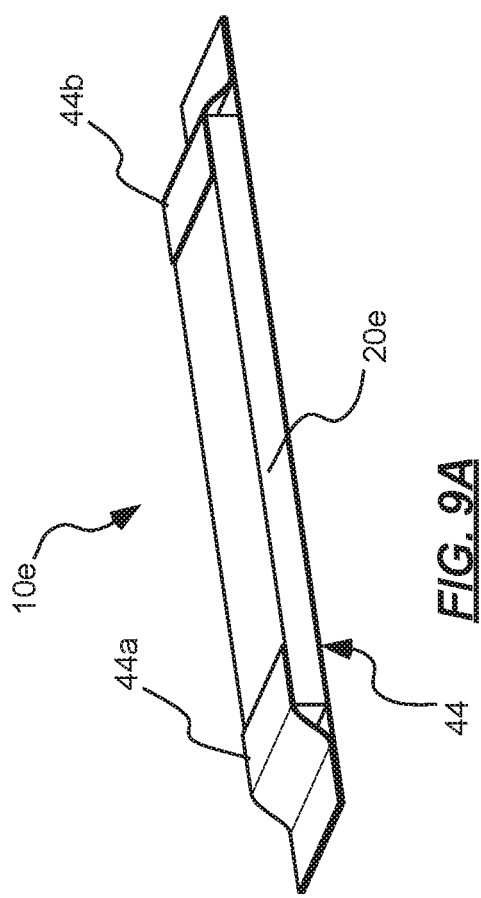
FIG. 9A is a perspective view of another cleaning assembly in accordance with the present technology.
Figure 9B:
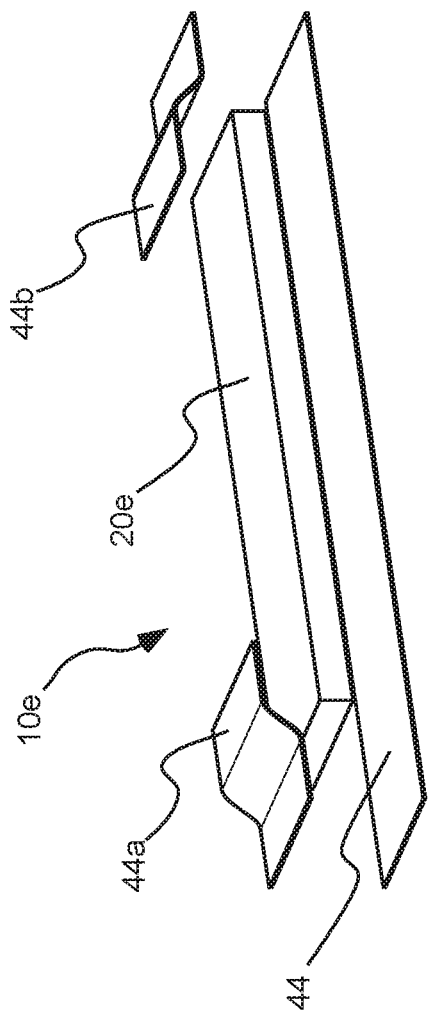
FIG. 9B is an exploded view of the assembly of FIG. 9A.

In the examples shown in FIGS. 9A and 9B, a cleaning assembly 10e is provided that can include one or more cleaning segments 20e arranged in a generally planar configuration (that is, the cleaning segment can be provided in a planar configuration prior to installation about a surgical instrument). In the embodiment shown, two shields or transitional segments 44a, 44b are positioned at either end of the cleaning segment. An adhesive layer 44 can be arranged beneath the cleaning segment and shields. A portion of each shield can be bonded to the adhesive layer, while the remaining portion of each shield can cover a portion of the cleaning segment.

In the embodiments illustrated in FIGS. 7A through 9B, the assembly may not completely encompass the secondary surgical instrument. In one embodiment, the assembly may "wrap" about the secondary surgical instrument only between 100 and 180 degrees of the available outer surface of the secondary surgical instrument.

The shields or transitional segments can be formed in a variety of manners and from a variety of materials. In one aspect, the transitional segments are much thinner and/or exhibit a much lower coefficient of friction than do the cleaning segments. This can aid in sliding the cleaning segments into and out of a trocar, for example. In one aspect, the shields can be formed from a thin, flexible material such as polyurethane, or a molded polymer such as a thermoplastic. The shields can also be formed from compressed segments of the cleaning segments. In one aspect, the cleaning segments can be formed with a thickness on the order of 0.057 inches, while the shield or transitional segments include a thickness of about 0.003 inches. These dimensions have been found to function well with a second surgical instrument having an outer diameter of about 0.209 inches.

In the examples shown in FIGS. 10A through 11, a cleaning assembly 10f is provided in which one or both cleaning segments 18e and 20e are formed with engagement features that can aid in grasping and manipulating the segment. The engagement features can take a variety of forms, but in the embodiment shown they include a notch 52 and/or peak 50. The peak that is thereby defined provides a tab 26e that can easily be engaged by a user to maneuver the cleaning assembly. As shown in FIG. 11, the tab 26e is maintained even when the cleaning assembly is installed about second surgical instrument 14. The notch remains defined adjacent the second surgical instrument even after the cleaning assembly is installed about the second surgical instrument.

In addition to the structural features discussed above, the present technology also provides various methods of manufacturing, forming, using and positioning cleaning assemblies. In one example, a method is provided of forming an assembly for cleaning a surgical instrument. The method can include obtaining a first cleaning segment and a second cleaning segment. The first and second cleaning segments can present a respective first and second cleaning interface configured to be contacted by a first surgical instrument to clean a portion of the first surgical instrument. The first cleaning interface can differ from the second cleaning interface so as to provide at least two differing cleaning interfaces for cleaning the first surgical instrument. The method can include coupling the first cleaning segment to the second cleaning segment to thereby define an instrument receiving channel between the first and second cleaning segments. The instrument receiving channel can be sized and shaped to receive therein a second surgical instrument to thereby secure the first and second cleaning segments to the second surgical instrument.

In one embodiment, the method can include bonding edges of the first cleaning segment to opposing edges of the second cleaning segment. In another example, the method can include plastically welding edges of the first cleaning segment to opposing edges of the second cleaning segment. The method can further include applying a buffer layer to an inside surface of one of the first or second cleaning segments. A material property of the first cleaning segment can differ from a material property of the second cleaning segment in at least one of: a porosity, a toughness, an abrasiveness, a radiopacity and a hardness.

It is to be understood that the above-referenced arrangements are illustrative of the application for the principles of the present invention. Numerous modifications and alternative arrangements can be devised without departing from the spirit and scope of the present invention while the present invention has been shown in the drawings and described above in connection with the exemplary embodiments(s) of the invention. It will be apparent to those of ordinary skill in the art that numerous modifications can be made without departing from the principles and concepts of the invention as set forth in the examples.

We claim:

1. An assembly for cleaning a surgical instrument, the assembly comprising:
   a first cleaning segment;
   a second cleaning segment, coupled to the first cleaning segment;
   the first and second cleaning segments presenting a respective first and second cleaning interface configured to be contacted by a first surgical instrument to clean a portion of the first surgical instrument;
   the first and second cleaning segments collectively defining an instrument receiving channel sized and shaped to receive therein a second surgical instrument to thereby secure the first and second cleaning segments to the second surgical instrument;
   a buffer layer disposed on an inside surface of at least one of the first and second cleaning segments, the buffer layer positioned so as to contact the second surgical instrument when the second surgical instrument is positioned within the instrument receiving channel; and
   at least one tab extending from the buffer layer, the tab providing an interface for a user to grasp the buffer layer.

2. The assembly of claim 1, wherein the first cleaning interface differs from the second cleaning interface so as to provide at least two differing cleaning interfaces for cleaning the first surgical instrument.

3. The assembly of claim 1, wherein the first and second cleaning segments exhibit differing material properties.

4. The assembly of claim 3, wherein a material property of the first cleaning segment differs from a material property of the second cleaning segment in at least one of: a porosity, a toughness, an abrasiveness, a radiopacity and a hardness.

5. The assembly of claim 1, wherein the instrument receiving channel is slidably positionable along the second surgical instrument.

6. The assembly of claim 1, wherein a material of at least one of the first and second cleaning segments is in direct contact with the second surgical instrument.

7. An assembly for cleaning a surgical instrument, the assembly comprising:
   a first cleaning segment;
   a second cleaning segment, coupled to the first cleaning segment;
   the first and second cleaning segments presenting a respective first and second cleaning interface configured to be contacted by a first surgical instrument to clean a portion of the first surgical instrument, the first cleaning interface differing from the second cleaning interface so as to provide at least two differing cleaning interfaces for cleaning the first surgical instrument;
   the first and second cleaning segments collectively defining an instrument receiving channel sized and shaped to receive therein a second surgical instrument to thereby secure the first and second cleaning segments to the second surgical instrument;
   a buffer layer disposed on an inside surface of at least one of the first and second cleaning segments, the buffer layer positioned so as to contact the second surgical instrument when the second surgical instrument is positioned within the instrument receiving channel; and
   at least one tab extending from the buffer layer, the tab providing an interface for a user to grasp the buffer layer;
   wherein a material of at least one of the first and second cleaning segments is in direct contact with the second surgical instrument.

8. The assembly of claim 7, wherein the first and second cleaning segments exhibit differing material properties.

9. The assembly of claim 8, wherein a material property of the first cleaning segment differs from a material property of the second cleaning segment in at least one of: a porosity, a toughness, an abrasiveness, a radiopacity and a hardness.

10. The assembly of claim 7, wherein the instrument receiving channel is slidably positionable along the second surgical instrument.

* * * * *